United States Patent
Phua et al.

(10) Patent No.: US 8,180,427 B2
(45) Date of Patent: May 15, 2012

(54) APPARATUS AND METHOD FOR NON-INVASIVELY SENSING PULSE RATE AND BLOOD FLOW ANOMALIES

(75) Inventors: Chee Teck Phua, Singapore (SG); Ming Hua Ying, Singapore (SG); See Hoon Kam, Singapore (SG); Boon Chong Gooi, Singapore (SG)

(73) Assignee: Nanyang Polytechnic, Singapore (SG)

( * ) Notice: Subject to any disclaimer, the term of this patent is extended or adjusted under 35 U.S.C. 154(b) by 886 days.

(21) Appl. No.: 12/162,607

(22) PCT Filed: Dec. 29, 2006

(86) PCT No.: PCT/SG2006/000409
§ 371 (c)(1),
(2), (4) Date: Jul. 30, 2008

(87) PCT Pub. No.: WO2007/097713
PCT Pub. Date: Aug. 30, 2007

(65) Prior Publication Data
US 2009/0203988 A1 Aug. 13, 2009

(30) Foreign Application Priority Data

Feb. 27, 2006 (SG) ................................ 200601301-5

(51) Int. Cl.
*A61B 5/05* (2006.01)
*A61B 5/021* (2006.01)
(52) U.S. Cl. ....................................... 600/407; 600/500
(58) Field of Classification Search .................. 600/407, 600/409, 419, 500–504; 324/306
See application file for complete search history.

(56) References Cited

U.S. PATENT DOCUMENTS

| | | | | |
|---|---|---|---|---|
| 2,149,847 A * | 3/1939 | Kolin | .......................... | 73/861.13 |
| 2,733,604 A * | 2/1956 | Coulter | ....................... | 73/861.12 |
| 3,191,119 A * | 6/1965 | Singer | ........................... | 324/306 |
| 3,419,793 A * | 12/1968 | Genthe et al. | ................. | 324/306 |
| 3,932,805 A * | 1/1976 | Abe et al. | ...................... | 324/309 |
| 4,079,730 A * | 3/1978 | Wikswo et al. | ............... | 600/504 |
| 4,202,350 A * | 5/1980 | Walton | .......................... | 600/503 |
| 4,205,688 A * | 6/1980 | Hauser et al. | ................. | 600/507 |
| 4,613,818 A * | 9/1986 | Battocletti et al. | ............ | 324/306 |
| 4,716,367 A * | 12/1987 | Patz | .............................. | 324/309 |
| 4,782,295 A * | 11/1988 | Lew | .............................. | 324/306 |
| 4,881,413 A * | 11/1989 | Georgi et al. | ............... | 73/861.12 |
| 5,794,622 A * | 8/1998 | Chopp et al. | .................. | 600/431 |
| 5,873,837 A * | 2/1999 | Lieber et al. | .................. | 600/504 |
| 6,438,402 B1 * | 8/2002 | Hashoian et al. | ............. | 600/410 |
| 6,856,832 B1 * | 2/2005 | Matsumura et al. | .......... | 600/523 |
| 6,910,382 B2 * | 6/2005 | Tang et al. | ...................... | 73/722 |

* cited by examiner

*Primary Examiner* — Francis Jaworski
(74) *Attorney, Agent, or Firm* — Pyprus Pte Ltd

(57) ABSTRACT

The present invention provides an apparatus and method for non-invasively sensing pulse rate and blood flow anomalies using a localized, uni-directional, and constant magnetic field. The apparatus comprises a magnetic source for producing the magnetic field, a signal acquisition module with a magnetic sensor for detecting the modulations of the magnetic field caused by the blood flow; and a signal processing module for processing the acquired signals so as to produce data of pulse rate and blood flow anomalies. The method senses pulse rate and blood flow anomalies by providing a localized, uni-directional, and constant magnetic field in proximity to a blood vessel; detecting the variations of the magnetic field caused by the flow of pulsatile blood within the blood vessel; and processing the signals of the detected variations so as to monitor the blood flow.

33 Claims, 10 Drawing Sheets where $h < g < f < e < d < c < b < a$ shows the occurrence of blood flow anomaly

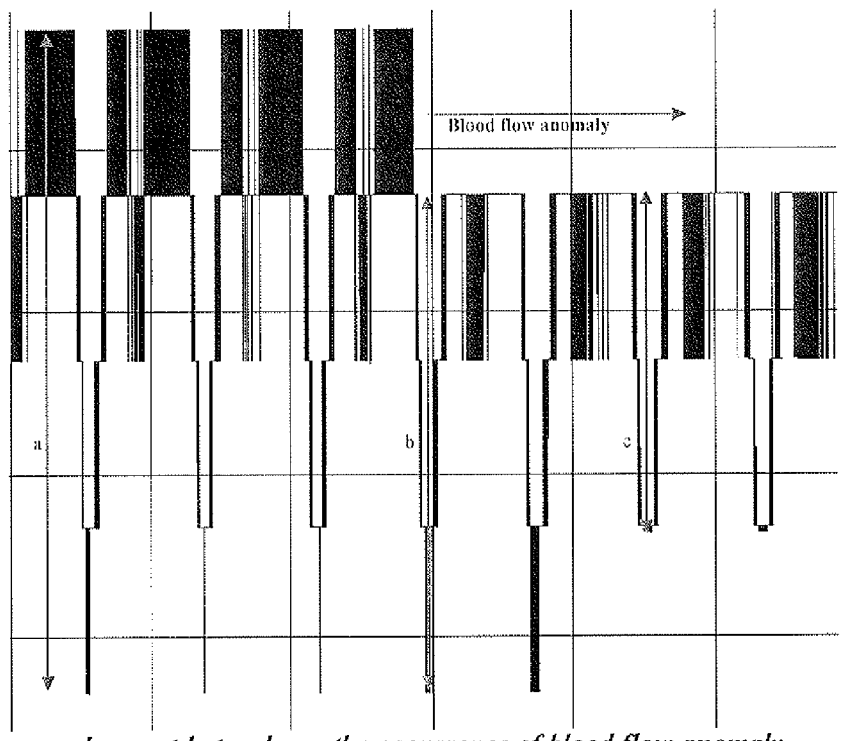
*where c < b < a shows the occurrence of blood flow anomaly*
FIG 8
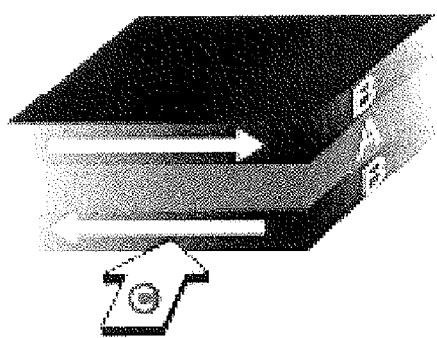
FIG 9a
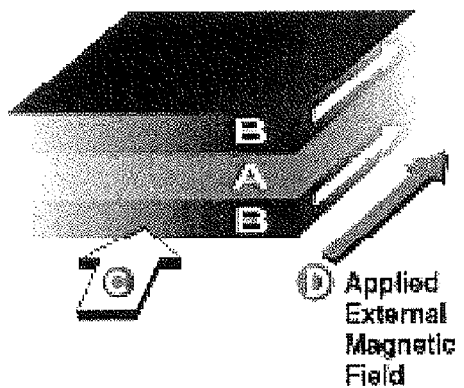
FIG 9b
FIG 9 (Prior Art)

APPARATUS AND METHOD FOR NON-INVASIVELY SENSING PULSE RATE AND BLOOD FLOW ANOMALIES

FIELD OF THE INVENTION

The present invention generally relates to apparatuses and methods for monitoring blood flows, and more particularly to an apparatus and method for non-invasively sensing pulse rate and blood flow anomalies using a localized, uni-directional, and constant magnetic field.

BACKGROUND OF THE INVENTION

With the advancement of bioelectronics, portable health monitoring devices are getting popular for they are able to provide continuous monitoring of an individual's health condition with ease of use and comfort. The portable health monitoring devices are increasingly used at places such as home, ambulance and hospital, and at situations including military training and sports.

Pulse rate and blood flow characteristics are important parameters subject to continuous monitoring because they are important in assessing the health condition of an individual. Healthcare institutes such as the hospitals and elderly care centres can use this information to remotely monitor the health conditions of their patients. This is particular important for paraplegic patients whose blood flow anomalies need to be detected early. In addition, blood flow anomaly monitoring for patients after major surgeries is important to ensure patients' smooth recovery.

Furthermore, pulse rate and blood flow information of individuals subjected to crowded and cramped conditions with limited physical activity may be utilized to trigger alert for immediate attention when blood flow anomalies, such as deep vein thrombosis, are detected. Similar monitoring and alert system may also be deployed during disaster where life condition of the affected personnel can be assessed continuously for rescue risk management. Finally, it is important for monitoring of the pulse rate and blood flow of personnel working in dangerous environments such as deep sea condition (divers), high temperature (fire-fighters), and deep underground (coal miners).

Current apparatuses for non-invasive measurements of blood pulse rate use electrical, mechanical and optical means for sensing. The apparatuses can come in the form of chest stripes, socks attachments, wrist-watches, and finger attachments. However, each of the apparatuses for blood pulse measurement has its weaknesses. Chest stripes and sock attachments usually measure the body electrical signals to determine the pulse rate; it is simple but requires the use of complex algorithms and/or reference signals to reduce noise due to motion artifacts. Measurement of pulse rate by mechanical means employs the detection of pulsation on the skin, which is highly susceptible to other motion artifacts. Optical means for pulse rate measurements usually come as finger attachment device. Such device employs the use of special light sources and detectors, which normally results in higher power consumption. With the various apparatuses discussed above, it is important to note that most of these apparatuses are not able to acquire information on blood flow.

Another type of apparatuses for measuring pulse rate and blood flow employs non-invasive electromagnetic method. For example, U.S. Pat. No. 5,935,077 discloses an electromagnetic blood flow sensor that uses a bipolar magnetic field source to provide a varying magnetic field with a component parallel to the skin and through the blood vessel, a single sense electrode on the skin adjacent to the blood vessel, a reference electrode, and a detector that samples the sense electrode signal in synchronism to the varying magnetic field. However, the non-invasive electromagnetic apparatuses using electrodes to measure pulse rate and blood flow have poor signal-to-noise ratios as most of the systems employ electrodes; the apparatuses are more susceptible to body electrical noise and motion artifacts. In addition, most of these apparatuses employ the reversal of magnetic field polarity to achieve signal acquisition of pulse rate and blood flow information. This method usually requires the use of an electromagnet, which will result in high power consumption. As such, the current electromagnetic apparatuses of pulse rate and blood flow monitoring are not portable and are not meant for ambulatory use.

SUMMARY OF THE INVENTION

Therefore, one embodiment of the present invention provides an apparatus for non-invasively monitoring of blood flow of an object including human. In the embodiment, the apparatus comprises a magnetic source for producing a localized, uni-directional, and constant magnetic field; and a signal acquisition module with a magnetic sensor disposed within the magnetic field for detecting the modulations of the magnetic field caused by the blood flow; a signal conditioning module for converting the output of the signal acquisition module with appropriate amplifications; and a digital signal processing module for processing the output signal from the signal conditioning module; thereby pulse rate and blood flow anomaly can be monitored. In another embodiment, the apparatus further comprises a display/userinterface/alarm module for providing visual or acoustic notification to a user.

In another embodiment of the apparatus, the magnetic source is a permanent magnet. In another embodiment of the apparatus, the magnetic source is an electromagnet. In yet another embodiment of the apparatus, the strength of the magnetic field produced by the electromagnet is controlled electronically.

In another embodiment of the apparatus, the magnetic source is preferably able to produce a magnetic field strength of 1000 Gauss±20% tolerance; wherein when the magnetic source is preferably able to produce a magnetic field strength of 1000 Gauss±20% tolerance, the magnetic source and magnetic sensor are separated by a distance of approximately 2.5 cm±20%.

In another embodiment of the apparatus, the magnetic sensor is any magnetic sensor with appropriate sensitivity of detecting the modulation of the magnetic field from the magnetic source. In yet another embodiment of the apparatus, the magnetic sensor is a Giant Magneto Resistance (GMR) magnetic sensor. In yet another embodiment of the apparatus, the magnetic sensor is a Spintronics based magnetic sensor. In yet another embodiment of the apparatus, the magnetic sensor is an anisotropic magnetoresistive sensor.

In another embodiment of the apparatus, the magnetic source and the magnetic sensor are preferably placed along the longitudinal axis of the blood vessel. In yet another embodiment of the apparatus, the magnetic source and sensor are placed at an offset position or angle with respect to the longitudinal axis of any major blood vessels near the surface of the skin.

In another embodiment of the apparatus, the signal conditioning module comprises an amplifier for amplifying the signals received from the signal acquisition module, and a signal digitization circuit for digitizing the received signals. In yet another embodiment of the apparatus, the signal conditioning module further comprises an optional envelope detector and/or filter using an analogue-to-digital converter (ADC).

In another embodiment of the apparatus, the signal processing module comprises a microcontroller, a microprocessor, a digital signal processor, programs to perform signal analysis, and a memory for storing all the programs and providing venues for the execution of the programs. In yet another embodiment of the apparatus, the pulse rate can be calculated with the following equation:

$$\text{Pulse rate} = \frac{n}{T} \times (60) \text{ pulses per minute}$$

where n is the number of pulses detected within the time duration T (in seconds); and T is the total time to observe n pulses.

In another embodiment of the apparatus, the magnetic source further comprises a placement mechanism controlling the placement of the magnetic source in respect to the signal acquisition module and the orientation of the blood vessel; thereby the placement of the magnetic source can be controlled. In yet another embodiment of the apparatus, the signal processing module further has the feedback capacities to control the signal for the placement mechanism and the signal for the sensitivity of the sensor in the signal conditioning module; in turn, the sensitivity control feedbacks to the signal acquisition module, and the placement mechanism feedbacks to the magnetic source to vary magnetic positions.

In another embodiment of the apparatus, the signal acquisition module further comprises a placement mechanism for a user to manually or automatically adjust the position and orientation of the magnetic sensor. In another embodiment of the apparatus, the display/userinterface/alarm module displays the two measurable parameters: blood flow anomaly and measured pulse rate. In another embodiment of the apparatus, the display/userinterface/alarm module comprises a display, an alarm, and a user interface.

In another embodiment, the apparatus further comprises a wireless interface module to allow remote monitoring; and a base station for receiving the information from the wireless interface module. In yet another embodiment of the apparatus, the base station comprises a data CODEC (Encoder and Decoder) and transceiver modules, display and user interface module, and microprocessor modules with RAM/ROM.

Another embodiment of the present invention provides a method for non-invasively monitoring of the blood flow of an object. In this embodiment, the method comprises providing a localized, uni-directional, and constant magnetic field in proximity to a blood vessel; detecting the variations of the magnetic field caused by the flow of pulsatile blood within the blood vessel; and processing the signals of the detected variations so as to monitor the blood flow.

In another embodiment of the method, the localized, uni-directional, and constant magnetic field is provided by a magnetic source that is a permanent magnet or an electromagnet. In yet another embodiment of the method, the variations of the magnetic field is detected by a signal acquisition module with a magnetic sensor. In yet another embodiment of the method, the magnetic sensor is a Spintronics based magnetic sensor or an anisotropic magnetoresistive sensor. In yet another embodiment of the method, the processing includes: converting the output of the signal acquisition module with appropriate amplifications by a signal conditioning module; and processing the output signal from the signal conditioning module to measure pulse rate and detect blood flow anomaly by a digital signal processing module.

In another embodiment of the method, the signal processing module comprises a microcontroller, a microprocessor, a digital signal processor, programs to perform signal analysis, and a memory for storing all the programs and providing venues for the execution of the programs. In yet another embodiment of the method, the pulse rate can be calculated with the following equation:

$$\text{Pulse rate} = \frac{n}{T} \times (60) \text{ pulses per minute}$$

where n is the number of pulses detected within the time duration T (in seconds); and T is the total time to observe n pulses.

In another embodiment of the method, the signal processing module detects the time interval between two adjacent pulses so as to measure and display physiological anomalies. In yet another embodiment of the method, the physiological anomalies include cardiac arrhythmia and on-set of heart failures.

One advantage of the present invention is that using magnetic field sensing to acquire the Modulated Magnetic Signature of Blood (MMSB) provides electrical isolation and is therefore less susceptible to body bioelectrical noise such as bioelectrical noise from the heart, brain and voluntary and involuntary motion artifacts.

Another advantage of the present invention is that it does not need to have direct physical contact of the magnetic source and/or signal acquisition module with the skin. For example, there could be fabric, perspiration and oil secretion between them. These do not in any way affect the quality of signal being acquired or measured. Another advantage of the present invention is that the use of a localised constant uni-directional magnetic field allows the employment of a permanent magnet. This will greatly reduce power consumption of the system making it feasible for deployment as a portable device.

Another advantage of the present invention is that the apparatus does not require a reference potential or signal such as the electrocardiogram (ECG). Another advantage of the present invention is that the apparatus can be designed and developed to automatically or manually optimize the data acquisition process by varying the strength of the magnetic field or the sensitivity of the sensor.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

FIG. 8 shows a typical digitized signal acquired with restricted blood flow on the heel at a more refined resolution.

FIG. 9a illustrates the working principle of a Spintronics based magnetic sensor with no external magnetic field.

FIG. 9b illustrates the working principle of a Spintronics based magnetic sensor with external magnetic field.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

In the following detailed description, specific details are set forth in order to provide a thorough understanding of the invention. However, it will be understood by those skilled in the relevant art that the present invention may be practiced without these specific details. In other instances, well-known methods, procedures, components, and materials have not been described in detail so as not to obscure the present invention.

The present invention provides an apparatus and method for non-invasively sensing pulse rate and blood flow in an object including human. The present invention is originated from the inventors' discovery that when a localized, unidirectional, and constant magnetic field is applied to a blood vessel, the flow of pulsatile blood can modulate the applied magnetic field and that the modulation of the magnetic field can be sensed directly if a magnetic sensor is disposed in a suitable position within the magnetic field. Of principle, the apparatus comprises a magnetic source for providing the magnetic field, a magnetic sensor for acquiring the signals of modulation, and a signal processing/displaying subunit for processing and outputting the processed signal. The processed signals, named modulated magnetic signature of blood (MMSB), are a function of the strength of the magnetic source, the sensitivity of the sensor, the distance between them, and their relative placement and orientation with respect to a major blood vessel near the surface of the skin.

While the following description will use specific configurations and dimensions and modules to illustrate the principles of the present invention, it by no means intends to limit the practice of the present invention to those specifics.

Figure 1:
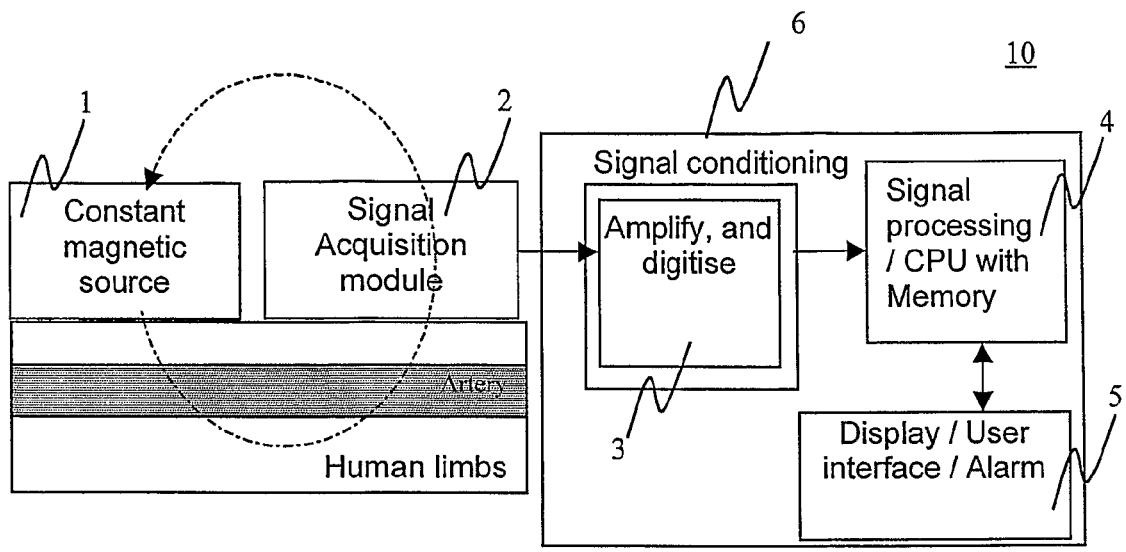
FIG. 1 is a functional block diagram of the non-invasive magnetic apparatus for sensing pulse rate and blood flow in an object in accordance with one embodiment of the present invention.

Now referring to FIG. 1, there is provided a functional block diagram of the non-invasive magnetic apparatus for sensing pulse rate and blood flow in an object in accordance with one embodiment of the present invention. The non-invasive magnetic apparatus 10 comprises a magnetic source 1, a signal acquisition module 2, and a signal processing/displaying subunit 6 including a signal conditioning module 3, a signal processing module 4, and a display/userinterface/alarm module 5. Briefly, a permanent magnet is shown in FIG. 1 to illustrate the magnetic field distribution near an artery and the signal acquisition module. The flow of pulsatile blood in the artery modulates the applied magnetic field to create a modulated magnetic signature of blood flow (MMSB). The MMSB is translated by the signal acquisition module to an electrical signal, which is then conditioned and digitized for signal processing. Then, the processed signal, primarily the pulse rate and blood flow profile, will be sent to the display/userinterface/alarm module.

The magnetic source 1 provides a localized, uni-directional, and constant magnetic field that is close to a major blood vessel. As discussed above, the flow of pulsatile blood modulates the applied magnetic field to produce a modulated magnetic signature of the blood flow (MMSB). The magnetic source 1 may comprise a permanent magnet, an electromagnet (including coil of wire, coil of wire on a ferromagnetic material, or coil of wire on a magnet), or the like as long as a constant magnetic field can be generated. The magnetic source may optionally further comprise a slider and control interface so as to control the position of the magnetic source within the apparatus. In addition, the magnetic source 1 may come in various geometry and sizes. As discussed hereinafter, a magnetic source may produce a magnetic field strength of 1000 Gauss±20% tolerance; that was used for the inventors' experiments. It is to be noted that the magnetic source may be of other magnetic field strength where the related parameters (e.g., the sensitivity of the sensor, the distance between the magnetic source and sensor, and the relative placement and orientation of the magnetic source and sensor with respect to a blood vessel) will have to be modified with appropriate support from experimental results.

The signal acquisition module 2 comprises a magnetic sensor that is able to translate magnetic variations to voltages proportional to the variations of the magnetic signature. The magnetic sensors suitable for the present invention include, but are not limited to, spintronics based sensors (e.g. giant magnetoresistive (GMR) sensor and tunneling magnetoresistive (TMR) sensor), anisotropic magnetoresistive (AMR) sensors and any magnetic based sensors. One exemplary magnetic sensor is a Spintronics based magnetic sensor (e.g., AAH002-02 manufactured by NVE Corporation). It is to be noted that other magnetic-based sensors with different sensitivities may also be used to detect the modulated magnetic signature of blood flow (MMSB), but the related parameters (e.g., the strength of the magnetic source, the distance between the magnetic source and sensor, and the relative placement and orientation of the magnetic source and sensor with respect to a blood vessel) will have to be modified with appropriate support from experimental results.

Figure 4:
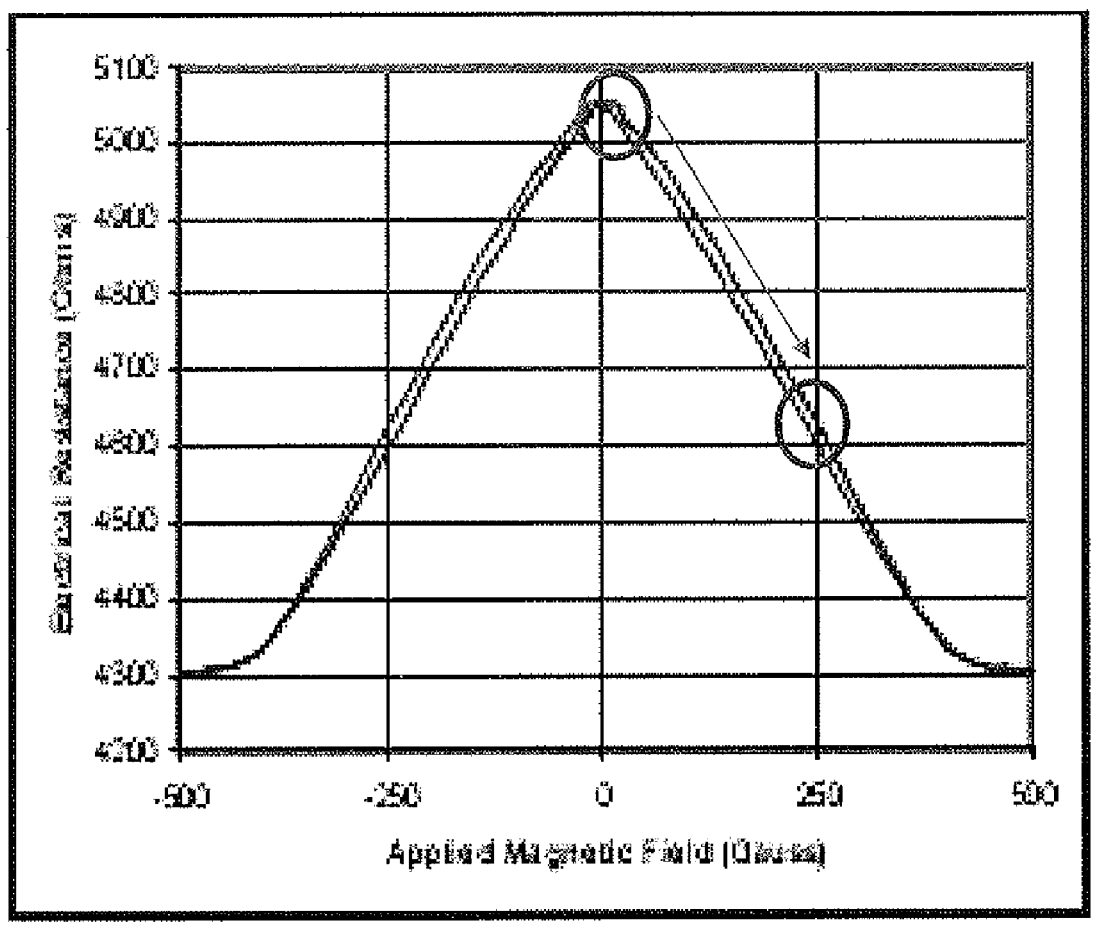
FIG. 4 is a graphic illustration of resistance change with respect to magnetic field applied.

Magnetic sensors are well known in the art. Their working principles will only be briefly described herein. Such sensors change their resistances based on the magnetic field applied. FIGS. 9a and 9b show a graphic illustration of the working principle behind the GMR magnetic sensors. As shown in FIG. 9a, a conductive, nonmagnetic interlayer A is sandwiched by two alloy layers B; when no external magnetic field is applied, the magnetic moments in the alloy layers face opposite directions (represented by the arrows), and the resistance to current C is high. As shown in FIG. 9b, when an external magnetic field D is applied, applied external magnetic field overcomes anti-ferromagnetic coupling, aligning magnetic moments in alloy layers, and the electrical resistance drops dramatically; 10% to 15% is typical. The magnetic signal variation is translated to a corresponding change of resistance in the GMR sensor device. This change of resistance with magnetic field applied can be illustrated as shown in FIG. 4. To those skilled in the art, the curve shows a change of resistance that can be correlated to minute variations in magnetic field.

Figure 2:
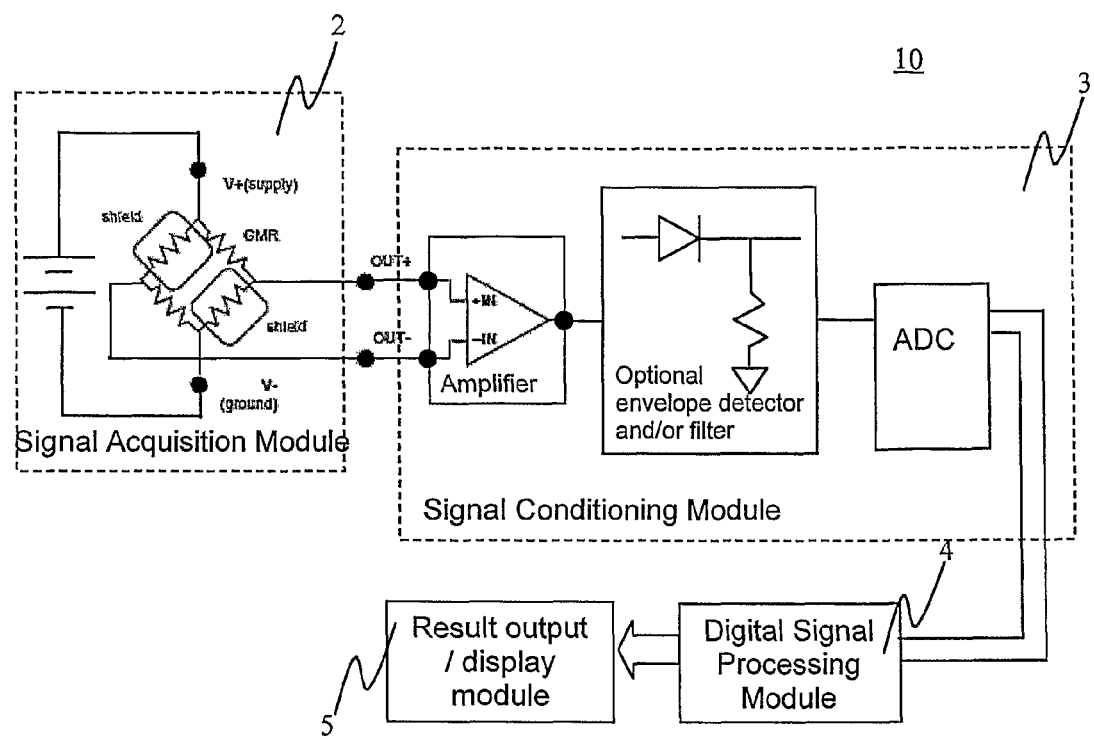
FIG. 2 shows exemplary schematic electronic circuits for the Signal Acquisition Module and the Signal Conditioning Module as shown in FIG. 1 in accordance with one embodiment of the present invention.

Now referring to FIG. 2, there is provided an exemplary schematic electronic circuit for the signal acquisition module 2 in accordance with one embodiment of the present invention. The circuit of the signal acquisition module 2 is so configured that a direct current (DC) power supply such as a battery to create a potential across the Wheatstone-Bridge connected to the GMR sensor. Coupled with the use of a Wheatstone-Bridge, the change in resistance due to the minute variations in the magnetic field can be translated into a measurable potential. To those skilled in the art, the potential applied across V+ and V− will result in a measured output across OUT+ and OUT−. The changes in resistance due to the applied magnetic field will then be linearly translated to a differential potential change across OUT+ and OUT−. Acquiring and measuring this differential potential will allow the magnetic field variations due to MMSB to be quantified and processed for measuring pulse rates and detecting blood flow anomalies.

With the application of a localised, unidirectional, and constant magnetic source, the measurable range of the Spintronics based magnetic sensor is shifted as shown in FIG. 4. To those skilled in the art, this will provide better linearity for the sensor to detect the minute changes of magnetic field generated from the modulated magnetic signature of blood (MMSB).

For optimized measurement of pulse rates and detection of blood flow anomalies by the apparatus, the factors other than the strength of the magnetic source and the sensitivity of the magnetic sensor need to be considered. First is the placement and orientation of the magnetic source with respect to a blood vessel. The magnetic source 1 may be preferably placed along the longitudinal axis of the blood vessel at an appropriate proximity that will generate a signal which can be detected by the magnetic sensor. In addition, the magnetic source may also be placed at an offset position or angle with respect to the longitudinal axis of any major blood vessels near the surface of the skin. If so, then other parameters including the strength of the magnetic source, the sensitivity of the sensor, and the distance between the magnetic source and sensor will have to be modified with appropriate support from experimental results. Second is the distance between the magnetic source and sensor. The distance is affected by many factors including the strength of the magnetic source. For example, when the magnetic source is about 1000 Gauss, the distance between the magnetic source and sensor is about 2.5 cm±20%. When the magnetic source produces a magnetic field with different strengths, it is easy for those skilled in the art to determine the proper range within which the magnetic sensor can be disposed without undue experimentation.

Figure 1A:
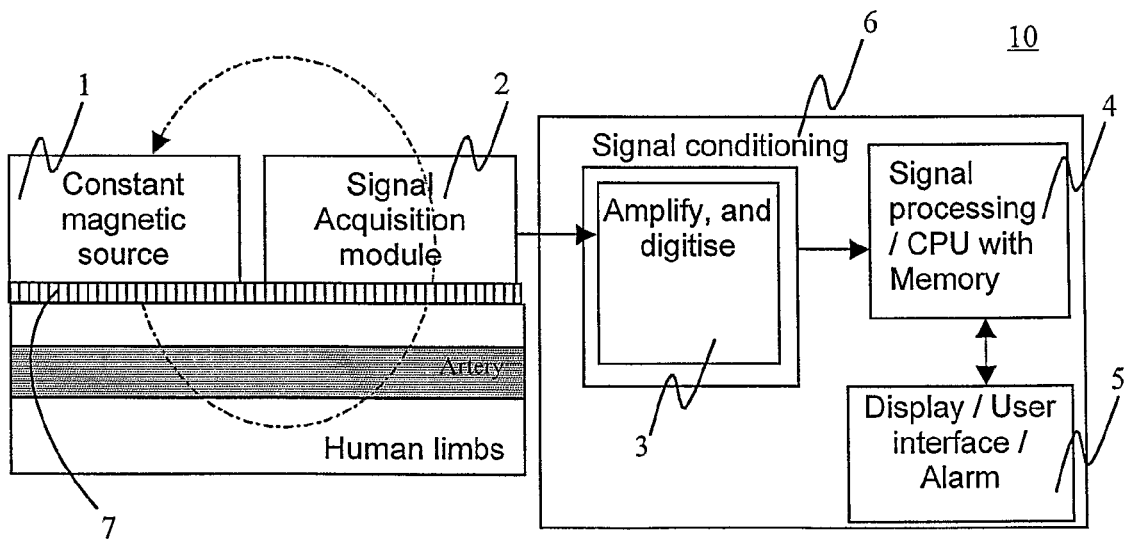
FIG. 1a shows a non-direct contact configuration for sensing pulse rate and blood flow using the non-invasive magnetic apparatus as shown in FIG. 1.

The magnetic source and magnetic sensor can sense the pulse rate and blood flow in a non-direct contact configuration. As shown in FIG. 1a, one space gap 7 may exist between the magnetic source/sensor and the skin. For example, the space gap could be fabric, perspiration and oil secretion between them. The thickness of the space gap can be easily determined in consideration of the strength of the magnetic source, the sensitivity of the magnetic sensor, and the material used in the space gap.

Now referring back to FIG. 1, the signal conditioning module 3 converts the differential-ended output of the signal acquisition module 2 into a single-ended signal with appropriate amplifications. In one embodiment, the signal conditioning module 3 comprises an amplifier for amplifying the signals received from the signal acquisition module, and a signal digitization circuit for digitizing the received signals. FIG. 2 shows an exemplary schematic circuit of the signal conditioning module 3. The suitable circuits are well known in the art. As shown in FIG. 2, an optional envelope detector and/or filter is proposed before digitization of the signal using an analogue-to-digital converter (ADC). To those skilled in the art, this will allow them to implement analogue signal selection before digitization.

Now referring to FIG. 1 and FIG. 2, the digital signal processing module 4 processes the digital signals from the signal conditioning module 3 to measure the pulse rate and detect blood flow anomaly. In one embodiment, the signal processing module 4 comprises a microcontroller, a microprocessor, a digital signal processor, programs to perform signal analysis, and a memory for storing all the programs and providing venues for the execution of the programs. The result output /display module 5 displays the two measurable parameters—blood flow anomaly and measured pulse rate—obtained from the digital signal processing module 4 in either discrete (LED) or continuous form (LCD). In one embodiment, the result output/display module 5 comprises a display, an alarm, and a user interface.

Figure 5:
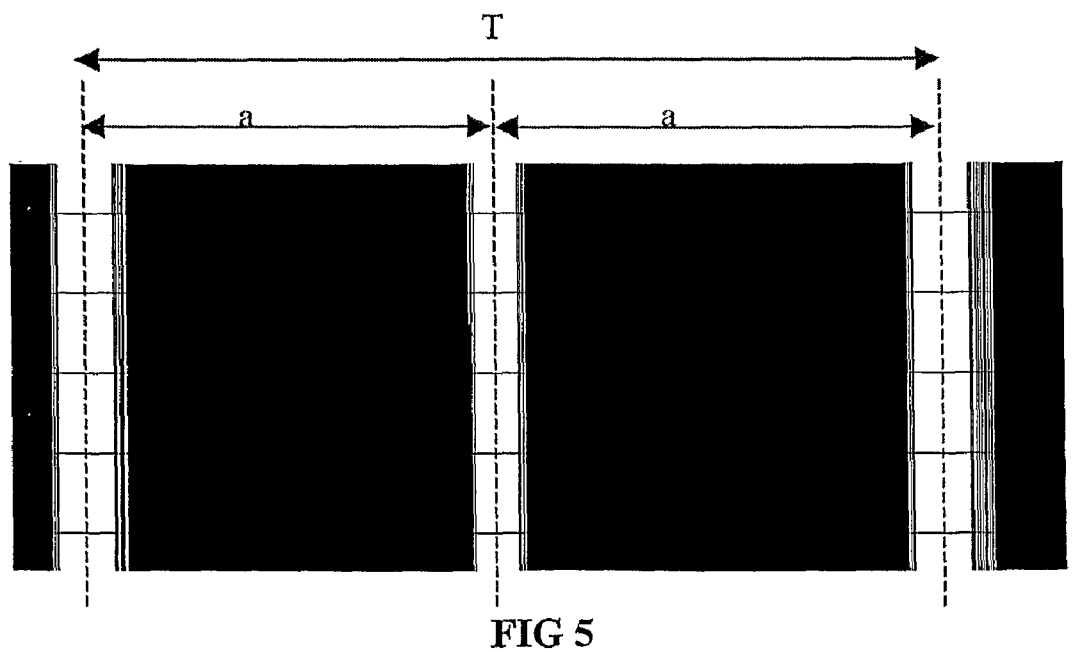
FIG. 5 shows a typical digitized signal acquired with normal blood flow on the wrist.
Figure 6:
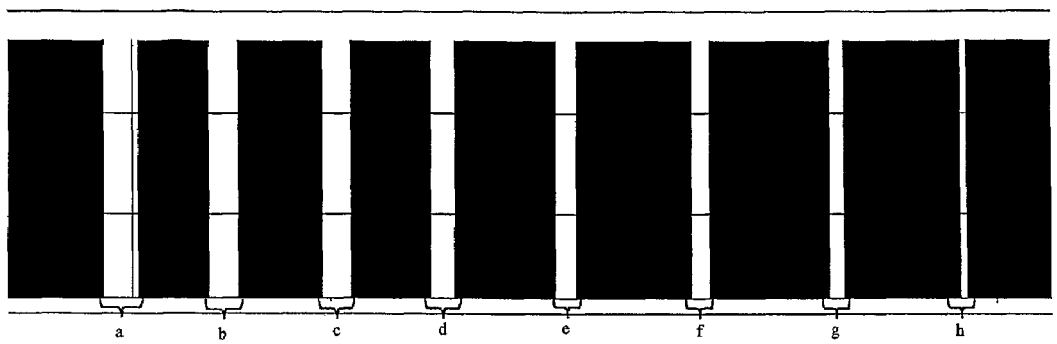
FIG. 6 shows a typical digitized signal acquired with restricted blood flow on the wrist.
Figure 7:
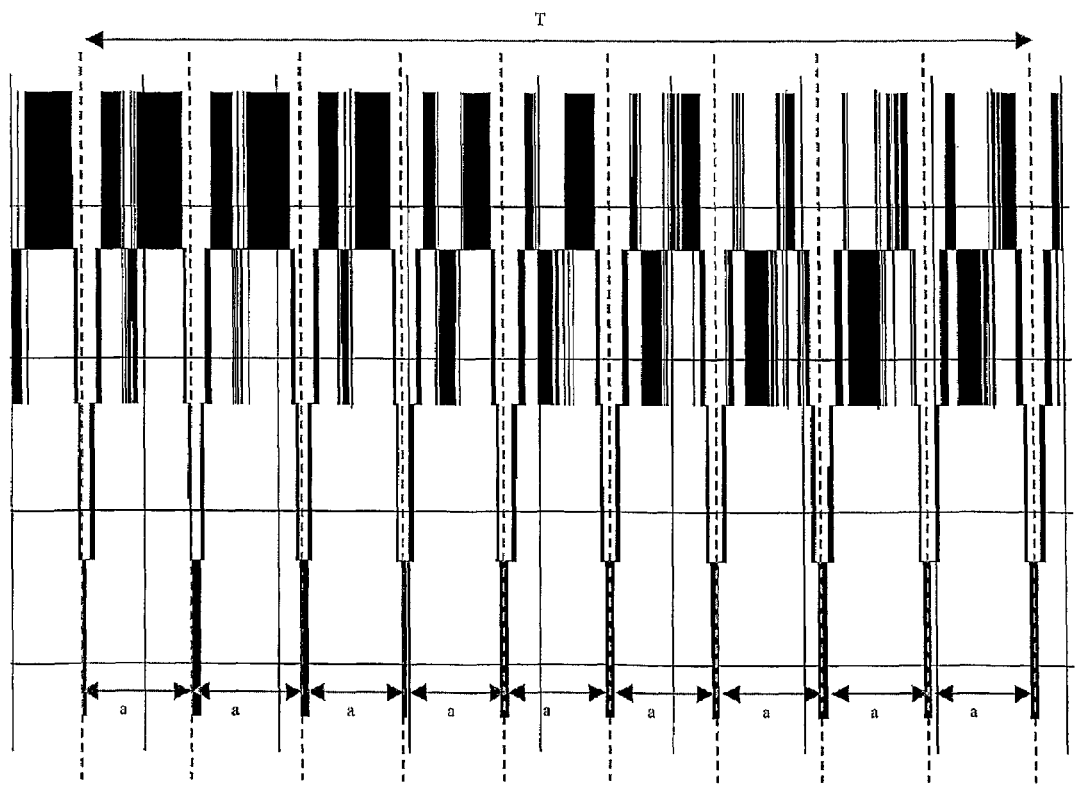
FIG. 7 shows a typical digitized signal acquired with normal blood flow on the heel at a more refined resolution.

The outputs may take different forms. For example, the outputs may be an alarm notification if any anomalies are detected. The pulse rates may be expressed as pulses per minute. The outputs may also be digital data with computed pulse rates. Typical digital data are shown in FIG. 5 and FIG. 6 for normal and abnormal blood flow condition respectively. Typical digital data are shown in FIG. 7 and FIG. 8 (at a more refined resolution) for normal and abnormal blood flow condition respectively. The calculation of pulse rates from the digital data will be discussed hereinafter.

Figure 3:
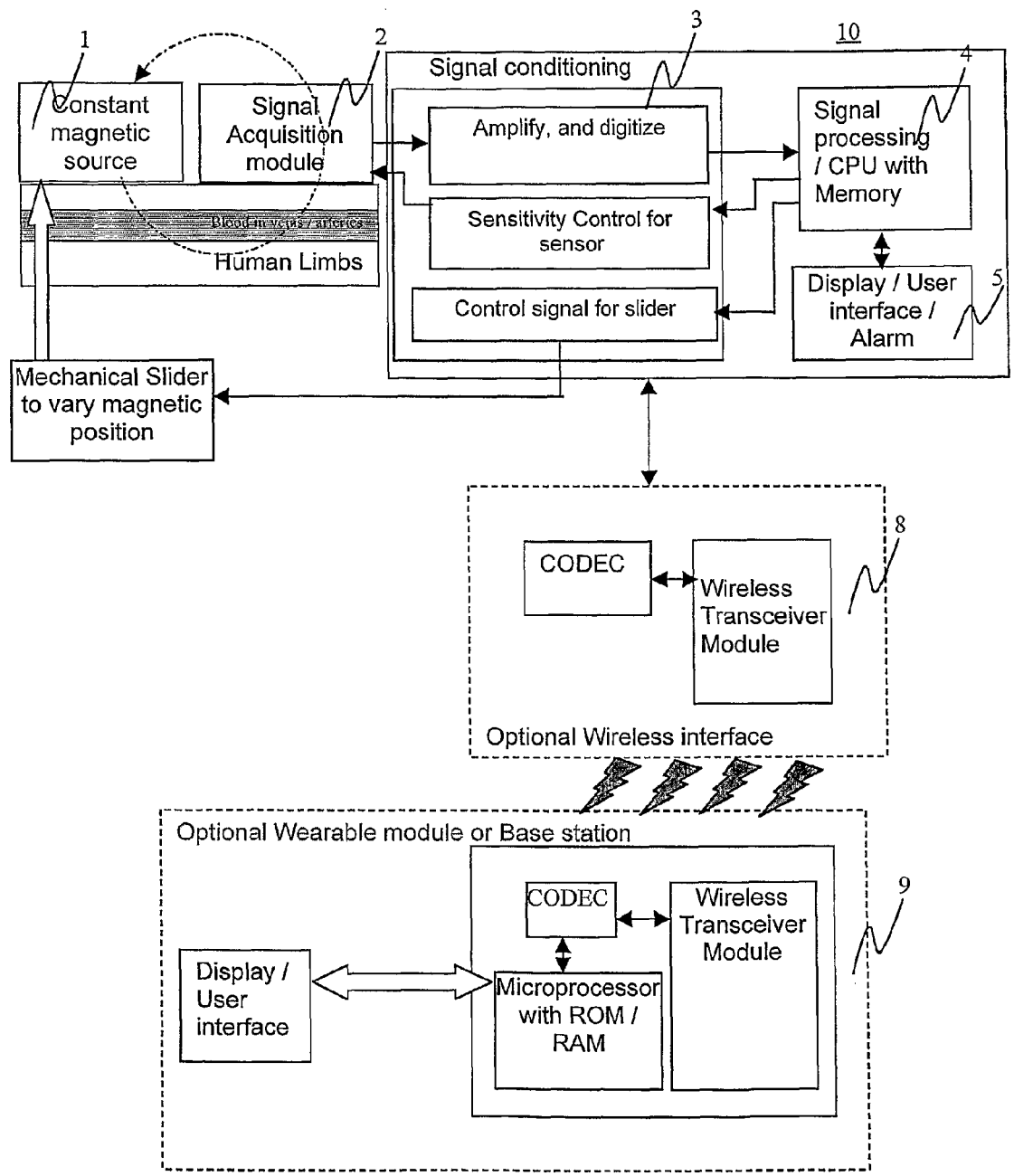
FIG. 3 is a functional block diagram of the non-invasive magnetic apparatus for sensing pulse rate and blood flow in accordance with another embodiment of the present invention.

Now referring to FIG. 3, there is provided a functional block diagram of the non-invasive magnetic apparatus that is able to automate signal acquisition to achieve optimal signal level. As shown in FIG. 3, the signal processing module 4 now has the feedback capacities to control the sensitivity of the sensor and placement mechanism such as a slider in the signal conditioning module. The placement mechanism enables a user to manually or automatically adjust the position and orientation of the magnetic source. In turn, the sensitivity control feedbacks to the signal acquisition module, and the slider control feedbacks to the magnetic source to vary magnetic positions. While not shown in FIG. 3, the signal acquisition module may further comprises a placement mechanism enabling a user to manually or automatically adjust the position and orientation of the magnetic sensor. In addition, while not shown in FIG. 3, the magnetic source may further comprise a strength adjustment mechanism when the electromagnet is used as the magnetic source. The devices for controlling position and orientation of the magnetic source and sensor and for controlling the strength of the magnetic source are well known to those in the arts; any suitable devices may be used in the present invention.

Still referring to FIG. 3, the apparatus further comprises a wireless interface module 8 to allow remote monitoring. The base station 9 may be incorporated into the apparatus or employed in a separate location for receiving the information from the apparatus. The base station comprises a data CODEC (Encoder and Decoder) and transceiver modules, display and user interface module, and microprocessor modules with RAM/ROM. The wireless transmission is well known in the art, thus no details will be provided herein.

Figure 10:
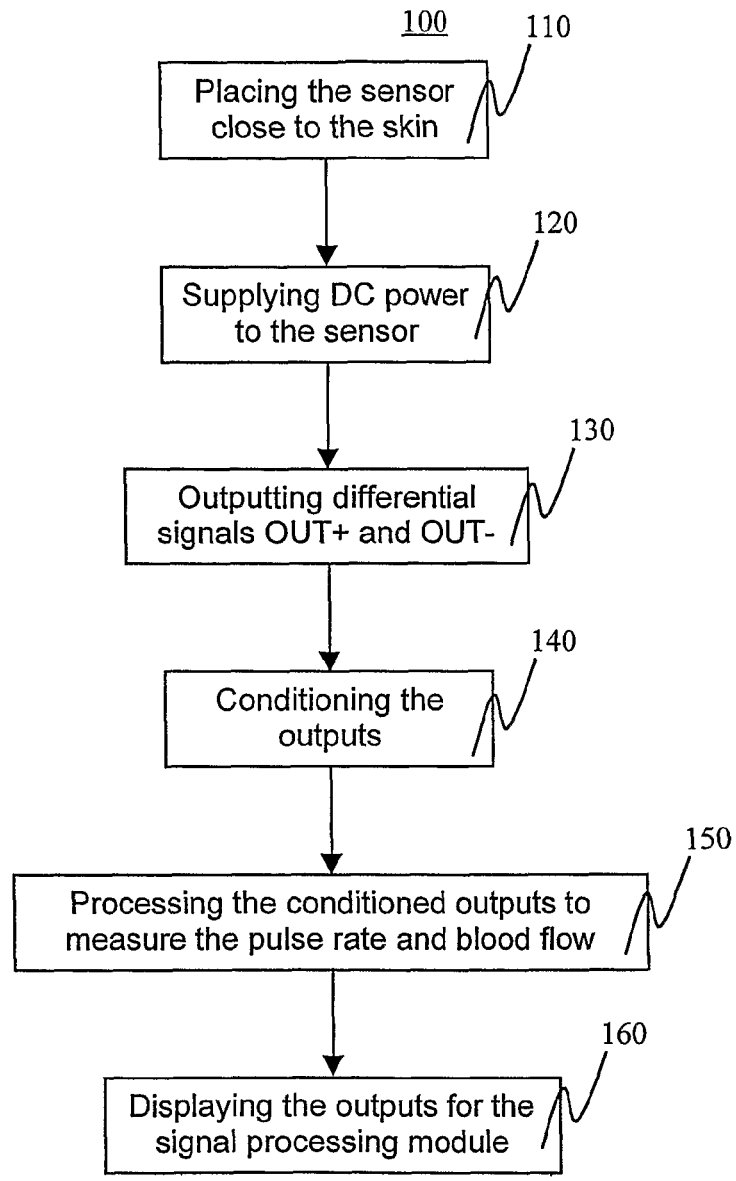
FIG. 10 is a flowchart of the method of sensing pulse rate and blood flow anomalies in accordance with one embodiment of the present invention.

Now referring to FIG. 10, there is provided a flow chart of the method for sensing the pulse rate and blood flow anomalies using a localized, uni-directional, and constant magnetic field.

The method 100 starts with placing directly or in proximity to the skin the apparatus for non-invasively sensing pulse rate and blood flow using the localized, uni-directional, and constant magnetic field 110. The magnetic source and sensor of the apparatus is preferably disposed along the longitudinal axis of a major blood vessel such as, but not limited to, the ones found on the wrist, leg, or heel.

Then, the sensor is then connected to a direct current (DC) power supply 120 such as a battery to create a potential across the Wheatstone-Bridge connected to the GMR sensor. For example, when the sensor used is the NVE AAH002-02, the potential applied is a DC voltage supply of 9V. Then, the signal acquisition module outputs the differential outputs, OUT+ and OUT−130.

Then, the output signals from the signal acquisition module are amplified by the signal conditioning module before any analogue signal conditioning (optional) 140. To those skilled in the art, such a configuration will ensure signal integrity. The analogue signal will then be digitised by the analogue-to-digital converter (ADC).

Then, the conditioned output signals from the signal conditioning module are processed by the signal processing module to measure the pulse rate and detect blood flow anomalies 150. Now referring to FIG. 5, there is provided a typical digital data acquired with normal blood flow on the wrist. The pulse rate can be calculated with the following equation:

$$\text{Pulse rate} = \frac{n}{T} \times (60) \text{ pulses per minute}$$

where n is the number of pulses detected within the time duration T (in seconds); a is the time interval between two adjacent pulses as shown in FIG. 5; and T is the total time to observe n pulses in seconds. The measurable parameter a can be used for the observation of heart beat anomaly such as the presence of a chaotic pattern which could signify the on-set of a heart attack or cardiac arrhythmia.

Then, the outputs from the signal processing module include pulse rate and blood flow anomalies. The outputs will be displayed 160 on the result output/display module.

The apparatus and method of the present invention is applicable to many situations. For example, hospitals can use the apparatus for monitoring patients; athletes can use the apparatus for monitoring their blood flow; elders can be monitored remotely with the wireless apparatus; blood flow anomalies can be detected in different circumstances such as long flight, rescues, and dangerous situations.

Figure 11:
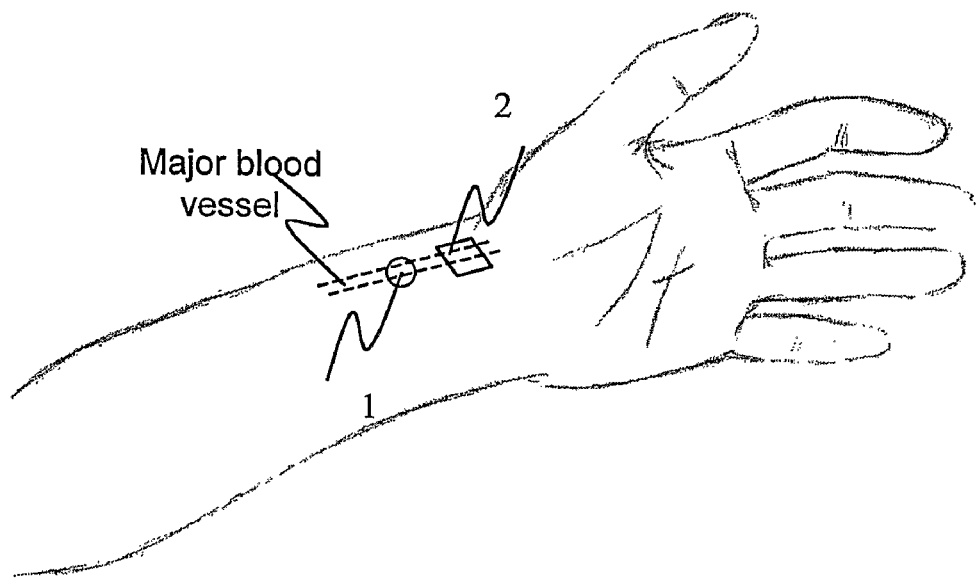
FIG. 11 shows a top view of hand with the non-invasive magnetic apparatus in accordance with one embodiment of the present invention.
Figure 12:
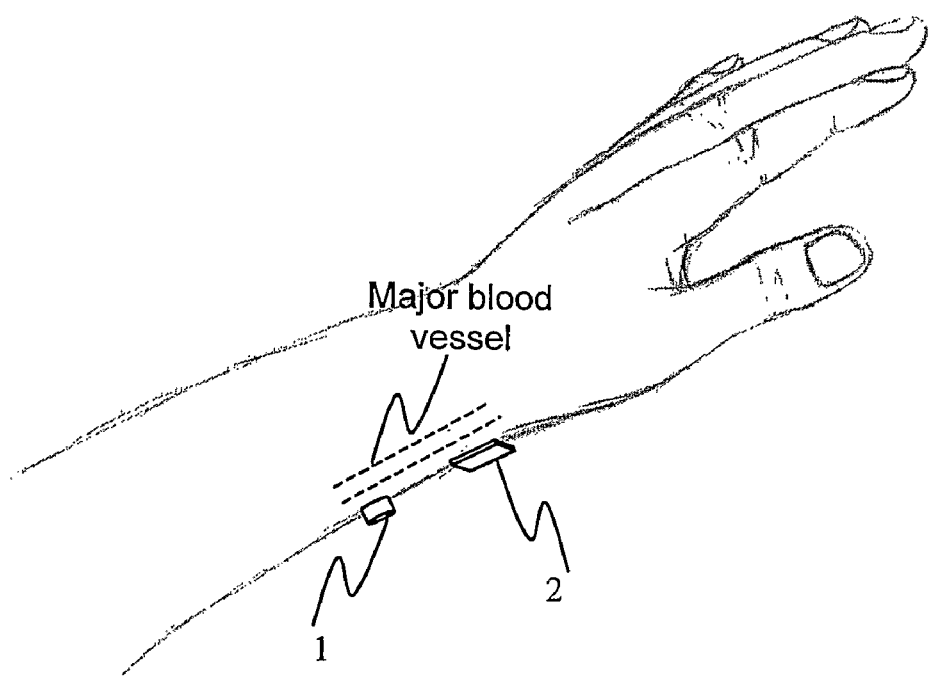
FIG. 12 shows a side view of hand with the non-invasive magnetic apparatus in accordance with one embodiment of the present invention.
Figure 13:
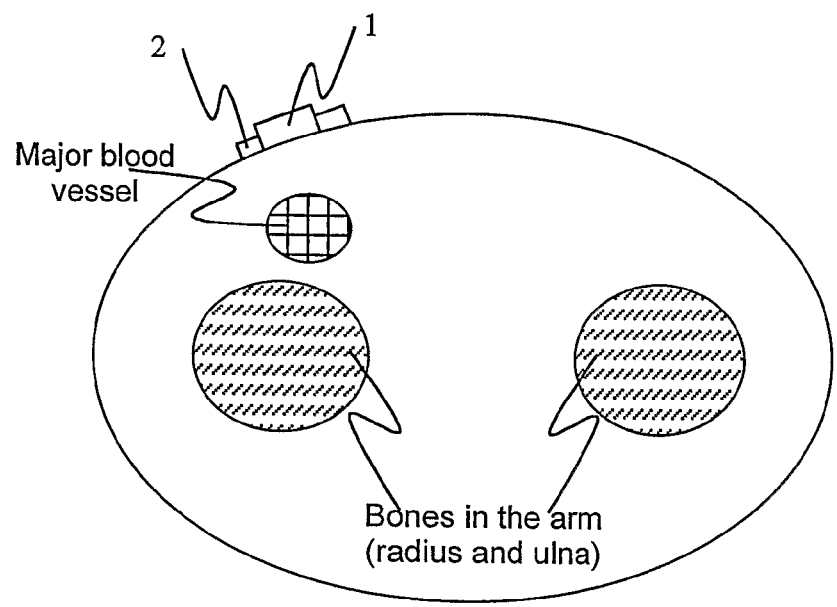
FIG. 13 shows a cross-section view of hand with the non-invasive magnetic apparatus in accordance with one embodiment of the present invention.

FIGS. 11-13 shows the placement and configuration of the non-invasive magnetic apparatus in accordance with one embodiment of the present invention. The magnetic source 1 and magnetic signal acquisition module 2 are placed along the longitudinal axis of the blood vessel on the wrist. In this design, the apparatus can be incorporated into any wrist wearing devices or decors. Of course, the apparatus can be used in other parts of a body and incorporated into other devices.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. An apparatus for non-invasively monitoring of blood flow of a living subject, comprising:
    a magnetic source for producing a localized, uni-directional, and constant magnetic field; and
    a signal acquisition module with a magnetic sensor, wherein the magnetic sensor is disposed within the magnetic field and detects the modulation of the localized uni-directional and constant magnetic field caused by the effect on the blood flow on said field in a blood vessel near the skin surface of the living subject;
    a signal conditioning module for converting the output of the signal acquisition module with appropriate amplifications; and
    a digital signal processing module for processing the output signal from the signal conditioning module;
    thereby pulse rate and blood flow anomaly can be monitored.

2. The apparatus of claim 1, further comprising a notification module for providing visual or acoustic notification to a user.

3. The apparatus of claim 2, wherein the notification module displays the two measurable parameters: blood flow anomaly and measured pulse rate.

4. The apparatus of claim 2, wherein the notification module comprises a display, an alarm, and a user interface.

5. The apparatus of claim 1, wherein the magnetic source is a permanent magnet.

6. The apparatus of claim 1, wherein the magnetic source is an electromagnet.

7. The apparatus of claim 6, wherein the strength of the magnetic field produced by the electromagnet is controlled electronically.

8. The apparatus of claim 1, wherein the magnetic source is preferably able to produce a magnetic field strength of 1000 Gauss±20% tolerance.

9. The apparatus of claim 8, wherein when the magnetic source is preferably able to produce a magnetic field strength of 1000 Gauss±20% tolerance, the magnetic source and magnetic sensor are separated by a distance of approximately 2.5 cm±20%.

10. The apparatus of claim 1, wherein the magnetic sensor is any magnetic sensor with appropriate sensitivity of detecting the modulation of the magnetic field from the magnetic source.

11. The apparatus of claim 10, wherein the magnetic sensor is a Giant Magneto Resistance (GMR) magnetic sensor.

12. The apparatus of claim 10, wherein the magnetic sensor is a Spintronics based magnetic sensor.

13. The apparatus of claim 10, wherein the magnetic sensor is an anisotropic magnetoresistive sensor.

14. The apparatus of claim 1, wherein the magnetic source and the magnetic sensor are placed along the longitudinal axis of the blood vessel.

15. The apparatus of claim 1, wherein the magnetic source and sensor are placed at an offset position or angle with respect to the longitudinal axis of the blood vessel.

16. The apparatus of claim 1, wherein the signal conditioning module comprises an amplifier for amplifying the signals received from the signal acquisition module, and a signal digitization circuit for digitizing the received signals.

17. The apparatus of claim 16, wherein the signal conditioning module further comprises an envelope detector and/or filter using an analogue-to-digital converter (ADC).

18. The apparatus of claim 1, wherein the signal processing module comprises a microcontroller, a microprocessor, a digital signal processor, programs to perform signal analysis, and a memory for storing all the programs and providing venues for the execution of the programs.

19. The apparatus of claim 18, wherein the microprocessor calculates the pulse rate with the following equation:

$$\text{Pulse rate} = \frac{n}{T} \times (60) \text{ pulses per minute}$$

where n is the number of pulses detected within the time duration T (in seconds); and T is the total time to observe n pulses.

20. The apparatus of claim 1, wherein the magnetic source further comprises a placement mechanism controlling the placement of the magnetic source in respect to the signal acquisition module and the orientation of the blood vessel; thereby the placement of the magnetic source can be controlled.

21. The apparatus of claim 20, wherein the signal processing module further has the feedback capacities to control the signal for the placement mechanism and the signal for a sensitivity control for sensor in the signal conditioning module; in turn, the sensitivity control feedbacks to the signal acquisition module, to control the sensitivity of the magnetic sensor, and the signal for the placement mechanism feedbacks to the magnetic source to vary magnetic positions.

22. The apparatus of claim 1, wherein the signal acquisition module further comprises a placement mechanism for a user to manually or automatically adjust the position and orientation of the magnetic sensor.

23. The apparatus of claim 1, further comprising:
a wireless interface module to allow remote monitoring the pulse rate and blood flow anomaly; and
a base station for receiving the information from the wireless interface module.

24. The apparatus of claim 23, wherein the base station comprises a data CODEC (Encoder and Decoder) and transceiver modules, display and user interface module, and microprocessor modules with RAM/ROM.

25. A method for non-invasively monitoring of the blood flow of a living subject using the apparatus of claim 1 an object, said method comprising the following operations:
providing a localized, uni-directional, and constant magnetic field in proximity to a blood vessel near the skin surface of a living object;
detecting the variations of the magnetic field caused by the flow of pulsatile blood within the blood vessel by a magnetic sensor disposed within the localized, unidirectional, and constant magnetic field; and
processing the signals of the detected variations so as to monitor the blood flow.

26. The method of claim 25, wherein the localized, uni-directional, and constant magnetic field is provided by a magnetic source that is a permanent magnet or an electromagnet.

27. The method of claim 25, wherein the magnetic sensor is part of a signal acquisition module for the detection of the variations of the magnetic field caused by the flow of pulsatile blood within the blood vessel.

28. The method of claim 27, wherein the magnetic sensor is a Spintronics based magnetic sensor or an anisotropic magnetoresistive sensor.

29. The method of claim 27, wherein the processing include:
converting the output of the signal acquisition module with appropriate amplifications by a signal conditioning module; and
processing the output signal from the signal conditioning module to measure pulse rate and detect blood flow anomaly by a digital signal processing module.

30. The method of claim 29, wherein the signal processing module comprises a microcontroller, a microprocessor, a digital signal processor, programs to perform signal analysis, and a memory for storing all the programs and providing venues for the execution of the programs.

31. The method of claim 29, wherein the pulse rate can be calculated with the following equation:

$$\text{Pulse rate} = \frac{n}{T} \times (60) \text{ pulses per minute}$$

where n is the number of pulses detected within the time duration T (in seconds); and T is the total time to observe n pulses.

32. The method of claim 29, wherein the signal processing module detects the time interval between two adjacent pulses so as to measure and display physiological anomalies.

33. The method of claim 32, wherein the physiological anomalies include cardiac arrhythmia and on-set of heart failures.

* * * * *

UNITED STATES PATENT AND TRADEMARK OFFICE
CERTIFICATE OF CORRECTION

PATENT NO.        : 8,180,427 B2                                     Page 1 of 1
APPLICATION NO.   : 12/162607
DATED             : May 15, 2012
INVENTOR(S)       : Chee Teck Phua et al.

It is certified that error appears in the above-identified patent and that said Letters Patent is hereby corrected as shown below:

Column 10, line 22, delete "uni-directional" and replace with "unidirectional"

Column 11, line 38, remove "," after module

Column 12, line 6, delete "object" and replace with "subject"

Signed and Sealed this
Fourteenth Day of August, 2012

David J. Kappos
*Director of the United States Patent and Trademark Office*